(12) United States Patent
Matsushita

(10) Patent No.: US 8,333,701 B2
(45) Date of Patent: Dec. 18, 2012

(54) ULTRASOUND DIAGNOSIS APPARATUS

(75) Inventor: Noriyoshi Matsushita, Mitaka (JP)

(73) Assignee: Hitachi Aloka Medical, Ltd., Mitaka-shi, Tokyo (JP)

(*) Notice: Subject to any disclaimer, the term of this patent is extended or adjusted under 35 U.S.C. 154(b) by 1080 days.

(21) Appl. No.: 12/166,644

(22) Filed: Jul. 2, 2008

(65) Prior Publication Data
US 2009/0012397 A1 Jan. 8, 2009

(30) Foreign Application Priority Data

Jul. 3, 2007 (JP) ................................ 2007-174793

(51) Int. Cl.
A61B 8/00 (2006.01)
(52) U.S. Cl. .................. 600/443; 600/407; 600/437
(58) Field of Classification Search .............. 600/508, 600/437, 407, 443, 510; 382/128
See application file for complete search history.

(56) References Cited

U.S. PATENT DOCUMENTS

| | | | |
|---|---|---|---|
| 5,322,067 A | 6/1994 | Prater et al. | |
| 5,465,721 A | 11/1995 | Kishimoto et al. | |
| 6,878,114 B2 | 4/2005 | Murashita | |
| 7,662,100 B2 | 2/2010 | Murashita | |
| 7,837,625 B2 | 11/2010 | Abe | |
| 2002/0123688 A1 | 9/2002 | Yamauchi | |
| 2003/0083578 A1* | 5/2003 | Abe et al. | 600/447 |
| 2004/0127794 A1* | 7/2004 | Murashita | 600/442 |
| 2005/0085729 A1* | 4/2005 | Abe | 600/450 |
| 2005/0267366 A1 | 12/2005 | Murashita et al. | |
| 2006/0074315 A1 | 4/2006 | Liang et al. | |
| 2006/0110050 A1* | 5/2006 | Aoyama et al. | 382/232 |

FOREIGN PATENT DOCUMENTS

| | | |
|---|---|---|
| JP | 2003-175041 A | 6/2003 |
| JP | 2004-24560 A | 1/2004 |
| JP | 2004-195082 A | 7/2004 |
| JP | 2004-202131 A | 7/2004 |
| JP | 2004-202132 A | 7/2004 |
| JP | 2005-124636 A | 5/2005 |
| JP | 2005-328948 A | 12/2005 |
| JP | 2005-334317 A | 12/2005 |
| WO | 2005/112773 A2 | 12/2005 |

OTHER PUBLICATIONS

European Office Action dated Aug. 26, 2009, issued in corresponding European Patent Application No. 08117195. European Search Report dated Oct. 13, 2008, issued in corresponding European Patent Application No. 08011719.5.
Chinese Office Action dated Mar. 3, 2010, issued in corresponding Chinese Patent Application No. 200810131875.X.
Japanese Office Action dated Mar. 6, 2012, issued in corresponding Japanese Patent Application No. 2007-174793.

* cited by examiner

Primary Examiner — Tse Chen
Assistant Examiner — Joel F Brutus
(74) Attorney, Agent, or Firm — Westerman, Hattori, Daniels & Adrian, LLP

(57) ABSTRACT

A parameter calculating unit calculates a parameter value at each time through an interpolation process based on a parameter value at a telediastole stored in a telediastole memory and a parameter value at a telesystole stored in a telesystole memory. An interpolation coefficient memory stores an interpolation coefficient which is used for the interpolation process. When the parameter calculating unit calculates, for each parameter, parameter values of the times from telediastole to the telesystole, a region-of-interest setting unit sets, for each time, a three-dimensional region of interest in the three-dimensional data space based on the plurality of parameters. With this process, a three-dimensional region of interest which dynamically changes from the telediastole to the telesystole is set in the three-dimensional data space.

8 Claims, 3 Drawing Sheets

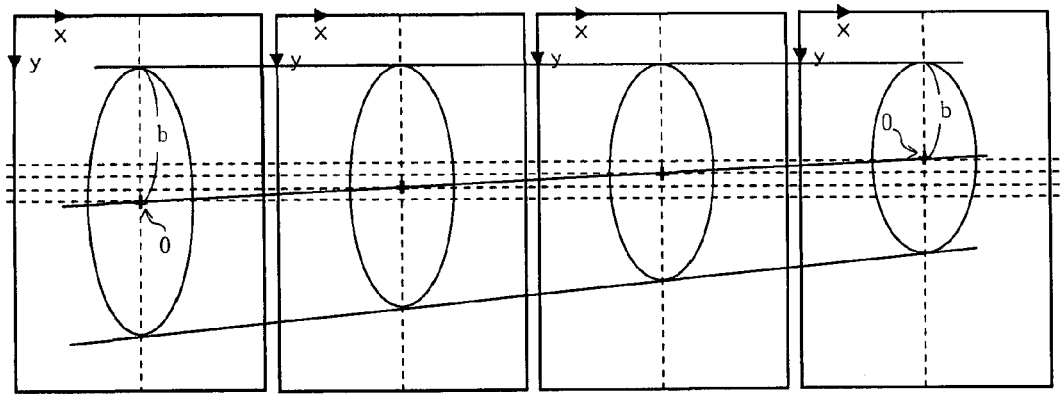
FIG. 2(a) TELEDIASTOLE    FIG. 2(b)    FIG. 2(c)    FIG. 2(d) TELESYSTOLE
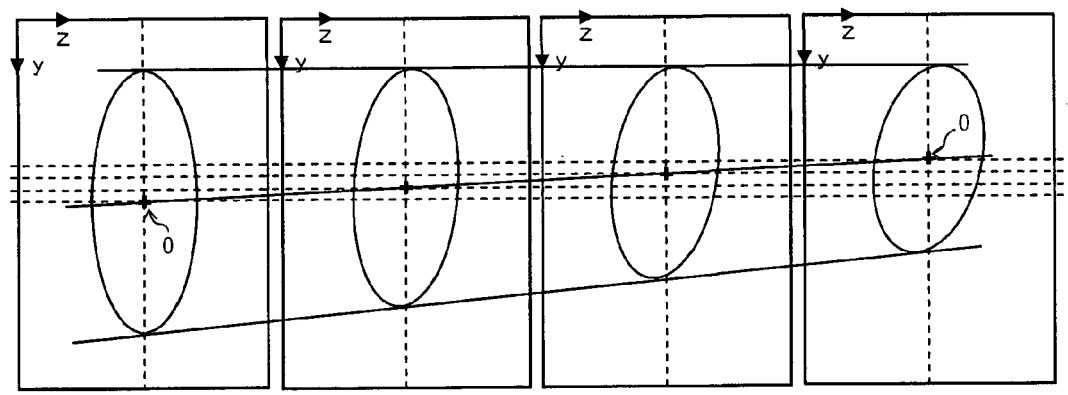
FIG. 3(a) TELEDIASTOLE    FIG. 3(b)    FIG. 3(c)    FIG. 3(d) TELESYSTOLE
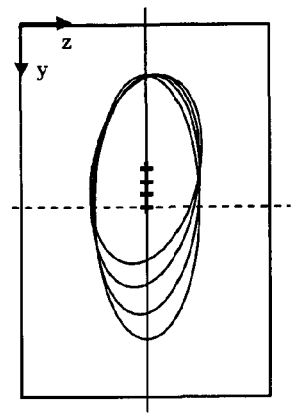
FIG. 3(f) : (a)~(d) ARE OVERLAPPED

ULTRASOUND DIAGNOSIS APPARATUS

BACKGROUND

1. Technical Field

The present invention relates to an ultrasound diagnosis apparatus, and in particular, to an ultrasound diagnosis apparatus in which a region of interest is set for a heart.

2. Related Art

An ultrasound diagnosis apparatus transmits and receives ultrasound to and from a space including a target site (such as, for example, an organ, a cavity within an organ, and a tumor), obtains echo data, and forms an ultrasound image such as a tomographic image and a three-dimensional image based on the echo data. In general, in the ultrasound image, an image of sites other than the target site is included, and a technique is known in which a region of interest is set for the target site, in order to improve the diagnosis precision or the like.

For example, Patent Document 1 (JP 2004-24560 A) discloses a technique in which a region of interest which is constantly superior can be adaptively set following a change of the target tissue such as a heart. Patent Document 2 (JP 2005-334317 A) discloses a technique in which a three-dimensional region of interest is set for three-dimensional image data.

For example, when an area or a volume of a cavity in a heart (cardiac cavity) is to be measured, a suitable setting of the region of interest for the heart would lead to an improvement in the measurement precision. However, suitable setting of the region of interest is not necessarily easy. For example, when a user sets a three-dimensional region of interest in a three-dimensional ultrasound image which three-dimensionally shows the heart or the like, the labor and time for the setting may be problematic. In particular, when the user is to set the three-dimensional region of interest to follow the expansion and contraction movement of the heart, even more labor and time would be required.

SUMMARY

The present invention was conceived in view of the above-described circumstances, and advantageously allows easy setting of a three-dimensional region of interest which dynamically follows the expansion and contraction movement of the heart.

In order to achieve at least the object described above, according to one aspect of the present invention, there is provided an ultrasound diagnosis apparatus comprising a transmission and reception unit which transmits and receives ultrasound, to collect a plurality of echo data from a three-dimensional space including a heart, an image forming unit which forms image data of a three-dimensional ultrasound image including the heart based on the plurality of collected echo data, a display unit which displays a three-dimensional ultrasound image corresponding to the formed image data, and a region-of-interest setting unit which sets a three-dimensional region of interest for a heart in a three-dimensional data space constructed by the plurality of echo data collected from the three-dimensional space, wherein the region-of-interest setting unit determines, for each parameter of a three-dimensional region of interest which is identified by a plurality of parameters, a parameter value at each time based on a parameter value corresponding to a telediastole of the heart and a parameter value corresponding to a telesystole of the heart.

According to this aspect of the present invention, for example, by the user setting the parameter value corresponding to the telediastole of the heart and the parameter value corresponding to the telesystole of the heart, it is possible to set the three-dimensional region of interest of the heart without requiring other complex operations or the like.

BRIEF DESCRIPTION OF THE DRAWINGS

Exemplary embodiment(s) of the present invention will be described in detail based on the following figures, wherein:

FIG. 2 is a diagram for explaining a three-dimensional region of interest which dynamically follows an expansion and contraction movement;

FIG. 3 is a diagram for explaining a three-dimensional region of interest which dynamically follows an expansion and contraction movement.

DETAILED DESCRIPTION

A preferred embodiment of the present invention will now be described with reference to the drawings.

Figure 1:
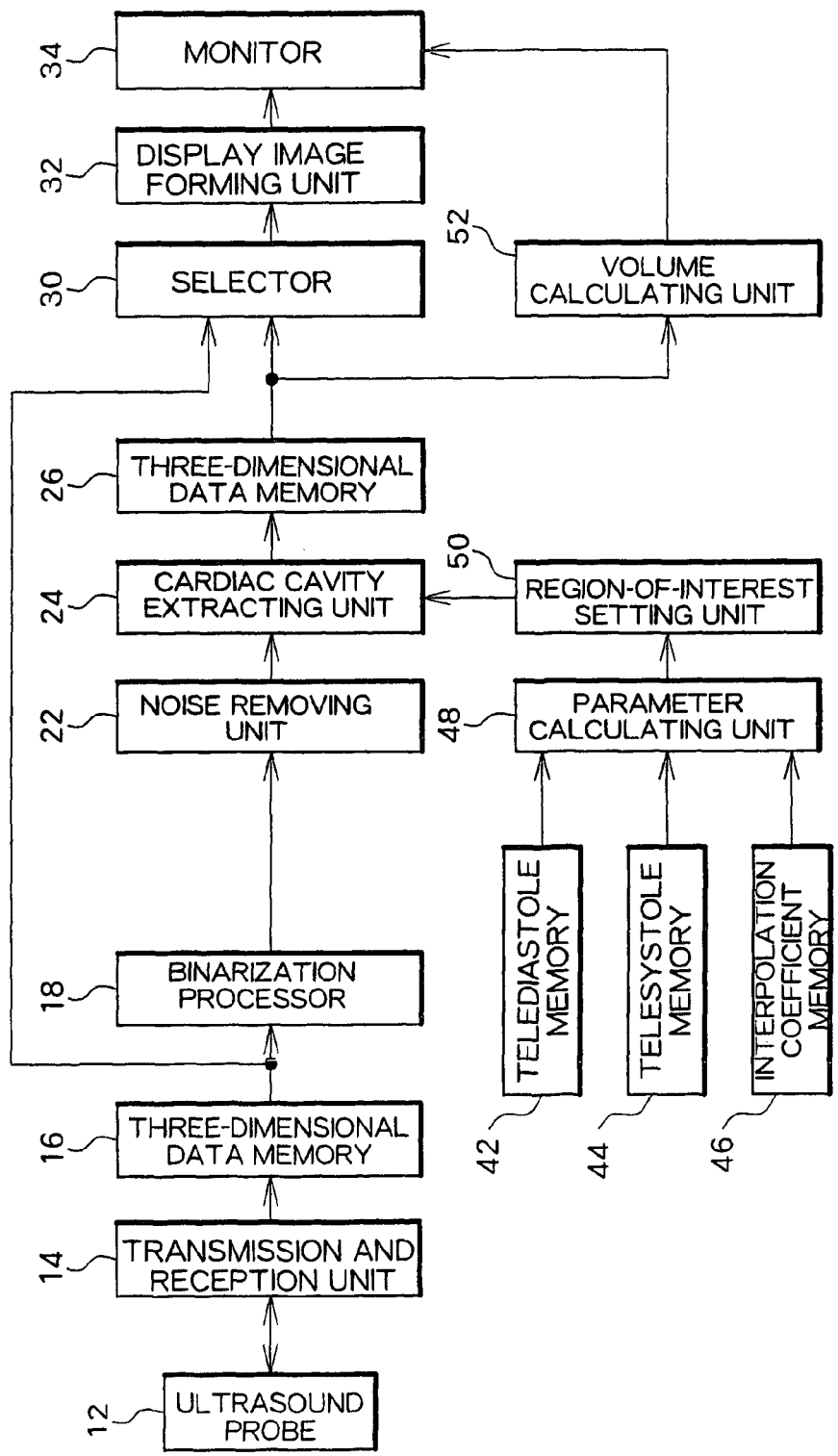
FIG. 1 is a functional block diagram showing an overall structure of an ultrasound diagnosis apparatus of a preferred embodiment of the present invention.

FIG. 1 shows a preferred embodiment of an ultrasound diagnosis apparatus according to the present invention. FIG. 1 is a functional block diagram showing an overall structure of the ultrasound diagnosis apparatus of the present embodiment. The ultrasound diagnosis apparatus of the present embodiment is suitable, for example, for diagnosis of a heart, and thus the present embodiment will be described with the heart as an example diagnosis target. The ultrasound diagnosis apparatus of the present embodiment can alternatively be applied to diagnosis of organs other than the heart.

An ultrasound probe 12 forms an ultrasound beam for a heart, and scans the ultrasound beam in a three-dimensional space including the heart. A transmission and reception unit 14 controls the ultrasound probe 12 to scan the ultra sound beam, to collect a plurality of echo data (three-dimensional data) from the three-dimensional space including the heart. The plurality of collected echo data are stored in a three-dimensional data memory 16.

If the ultrasound probe 12 is a convex type probe, the three-dimensional data is stored, for example, in an address in a three-dimensional data space corresponding to a polar coordinate system ($\theta$, $\phi$, r) with a main scan direction $\theta$ of the ultrasound beam, a sub-scan direction $\phi$ orthogonal to the main scan direction, and a distance r of a contact surface of the ultrasound probe from a center of curvature. The storage format of the three-dimensional data may alternatively be a format in which the data is converted from the polar coordinate system which is directly obtained from the information of the reflected wave to other coordinate systems such as, for example, a rectangular coordinate system (x, y, z). In other words, the three-dimensional data may be stored in an address in a three-dimensional data space corresponding to the rectangular coordinate system (x, y, z).

The data stored in the three-dimensional data memory 16 (three-dimensional data comprising a plurality of echo data) correspond to the brightness of the reflected wave (intensity of reflection), and, in the case where the diagnosis target is a heart, a site such as a heart wall having a high reflection has a high brightness, while a portion such as the cardiac cavity having a low reflection has a low brightness. In consideration of this, in a binarization processor 18, the echo data in the three-dimensional data memory 16 are separated into two values of a high level and a low level using a predetermined threshold value, so that the data is binarized to echo data of low brightness including the cardiac cavity and echo data of high brightness including the heart. The threshold value may be set in the apparatus in advance or may alternatively be set by a user according to the obtained ultrasound image.

A noise removing unit 22 executes a removal process of noise on the binarized three-dimensional data. For example, on a θ-φ plane, when brightness values of 5 echo data, among 8 peripheral echo data of certain echo data (echo data of interest), are high level, the value of the echo data of interest is set to the high level. When the number of brightness values of high level is less than 5, the brightness value of the echo data of interest is maintained. Similarly, when brightness values of 5 peripheral echo data are low level, the brightness value of the echo data of interest is set to low level, and the brightness value of the echo data is maintained when the number of brightness values of low level is less than 5. Although this noise removal process is executed on the θ-φ plane, the noise removal process may alternatively be executed on the θ-r plane or on the φ-r plane. Alternatively, the brightness value of the echo data of interest may be determined based on brightness values of 26 echo data three-dimensionally at a periphery of the echo data of interest. Alternatively, the noise removal process may be executed in the three-dimensional data space corresponding to the rectangular coordinate system (x, y, z).

A cardiac cavity extracting unit 24 extracts the cardiac cavity based on the binarized data after the noise process. For example, a cardiac cavity of a left ventricle is extracted. When the cardiac cavity of the left ventricle is to be extracted, although the echo data of the cardiac cavity is set to the low level by the binarization process, echo data corresponding to cardiac cavity in sites other than the left ventricle and other low-brightness sites are also at the low level. In other words, simple extraction of the echo data of the low level from the binarized three-dimensional data does not result in suitable extraction of the cardiac cavity of left ventricle. In consideration of this, in the present embodiment, a three-dimensional region of interest is set for a target site such as, for example, the cardiac cavity of the left ventricle.

In the present embodiment, the three-dimensional region of interest is identified by a plurality of parameters. By determining, for each parameter, a parameter value at each time based on a parameter value corresponding to a telediastole (end-diastole) of the heart and a parameter value corresponding to a telesystole (end-systole) of the heart, the plurality of parameters are changed with elapse of time so that the three-dimensional region of interest dynamically follows the expansion and contraction movement of the heart.

FIGS. 2 and 3 are diagrams for explaining a three-dimensional region of interest which dynamically follows the expansion and contraction movement. FIGS. 2 and 3 show a three-dimensional data space comprising a plurality of echo data (three-dimensional data) collected from a three-dimensional space including the heart, and a region of interest having a shape of an ellipsoid is set in the three-dimensional data space.

FIG. 2 corresponds to a front view (xy plane) of the three-dimensional data space represented by an xyz rectangular coordinate system. FIGS. 2(a)-2(d) show a change with elapse of time of the three-dimensional region of interest from a telediastole (a) of the heart to the telesystole (d) of the heart. As shown in FIG. 2, the length of the major axis radius b of the three-dimensional region of interest and the position of the center O of the ellipsoid change between the telediastole (a) of the heart and the telesystole (d) of the heart.

FIG. 3 corresponds to a side view (yz plane) of the three-dimensional data space represented by an xyz rectangular coordinate system. FIGS. 3(a)-3(d) show a change with elapse of time of the three-dimensional region of interest between the telediastole (a) of the heart and the telesystole (d) of the heart. As shown in FIG. 3, the position of the center O of the ellipsoid which is the three-dimensional region of interest and a rotation angle (for example, the rotation angle when the x-axis is the rotation axis) change between the telediastole (a) of the heart and the telesystole (d) of the heart. FIG. 3(f) shows the three-dimensional regions of interest (ellipsoids) of FIGS. 3(a)-3(d) in an overlapping manner.

As shown in FIGS. 2 and 3, for the three-dimensional region of interest having the ellipsoidal shape, by changing, with elapse of time, the parameters such as the length of the major axis radius b, position of the center O, and rotation angle, it is possible to change the position, angle, and size of the three-dimensional region of interest in the three-dimensional data space. In the present embodiment, by determining the parameter value at each time based on the parameter value at the telediastole of the heart and the parameter value at the telesystole of the heart, the three-dimensional region of interest which is identified by a plurality of parameters is set to dynamically follow the expansion and contraction movement of the heart.

Referring again to FIG. 1, a telediastole memory 42 and a telesystole memory 44 are memories for storing parameter values of the plurality of parameters for identifying the three-dimensional region of interest. The telediastole memory 42 stores the values of the parameters at the telediastole of the heart. Similarly, the telesystole memory 44 stores the values of the parameters at the telesystole of the heart.

When the three-dimensional region of interest has an ellipsoidal shape, preferable parameters as the plurality of parameters for identifying the size, position, and angle of the ellipsoidal shape are a minor axis radius a in the xy plane, a major axis radius b, a minor axis radius c in the zx plane, xyz coordinates of the center position (x0, y0, z0), rotation angle θx around the x-axis, rotation angle θy around the y-axis, and rotation angle θz around the z-axis. The telediastole memory 42 stores values of these parameters corresponding to the telediastole and the telesystole memory 44 stores values of these parameters corresponding to the telesystole.

The three-dimensional regions of interest corresponding to the telediastole and the telesystole are manually set. For example, a user causes an image corresponding to a front view of the heart at the telediastole (FIG. 2(a)) and an image corresponding to the side view of the heart at the telediastole (FIG. 3(a)) to be displayed on a monitor 34, and sets the region of interest having the ellipsoidal shape using an operation panel or the like (not shown). For example, the user sets the region of interest having the ellipsoidal shape surrounding the cardiac cavity of the left ventricle of the heart by suitably adjusting the size, position, and angle of the region of interest with the operation panel. The values of the parameters after this setting are registered in the telediastole memory 42.

Similarly, the user causes an image corresponding to a front view of the heart at the telesystole (FIG. 2(d)) and an image corresponding to a side view of the heart at the telesystole (FIG. 3(d)) to be displayed on the monitor 34, and sets the region of interest having the ellipsoidal shape surrounding the cardiac cavity of the left ventricle of the heart by suitably adjusting the size, position, and angle of the region of interest using the operation panel or the like (not shown). The values of the parameters after this setting are registered in the telesystole memory 44.

A parameter calculating unit 48 calculates, through an interpolation process, a parameter value at each time based on the parameter value at the telediastole stored in the telediastole memory 42 and the parameter value at the telesystole stored in the telesystole memory 44. An interpolation coefficient memory 46 stores an interpolation coefficient which is used for the interpolation process.

Figure 4:
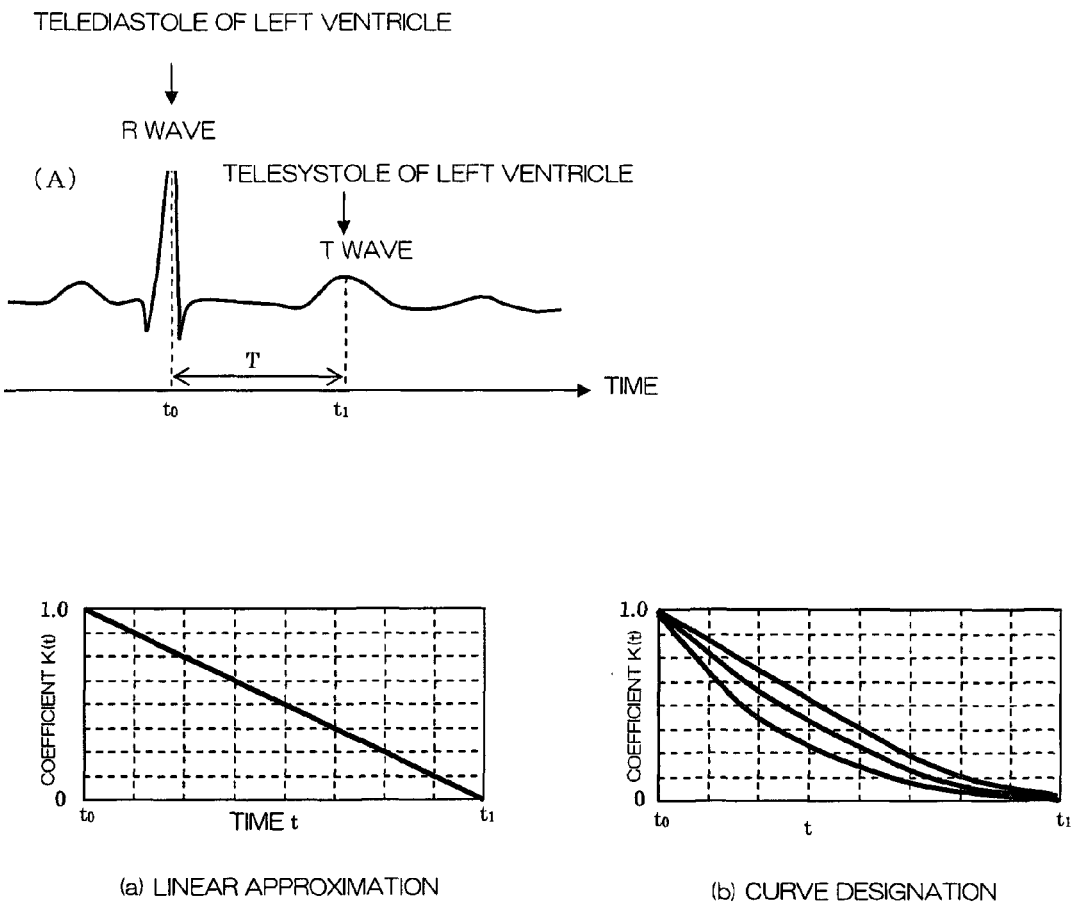
FIG. 4 is a diagram for explaining an interpolation process in a parameter calculating unit.

FIG. 4 is a diagram for explaining the interpolation process in the parameter calculating unit (reference numeral 48 in FIG. 1). FIG. 4(A) shows an electrocardiographic waveform of the heart. For example, the timings of the telediastole and the telesystole of the left ventricle of the heart are determined based on the electrocardiographic waveform. Specifically, the timing of appearance of an R wave in the electrocardiographic waveform is set as a time $t_0$ of the telediastole of the left ventricle and a timing of appearance of a T wave in the electrocardiographic waveform is set as a time $t_1$ of the telesystole of the left ventricle.

For each parameter, a parameter value at each time from the time $t_0$ the time $t_1$ is calculated through an interpolation process using the interpolation coefficient and based on a parameter value at the time $t_0$ and a parameter value at the time $t_1$. FIGS. 4(a) and 4(b) show the interpolation coefficients used in the interpolation process. The interpolation coefficient is a coefficient in which a mixture ratio of the parameter value corresponding to the telediastole and the parameter value corresponding to the telesystole is determined for each time.

For a certain parameter a (for example, a minor axis radius), if the parameter value at the time $t_0$ which is the time of the telediastole is at0, the parameter value at the time $t_1$ which is the time of the telesystole is at1, and the value of the interpolation coefficient at time t is k[t], the value a[t] of the parameter a at the time t is calculated based on the following formula.

$$a[t]=at1+k[t]\cdot(at0-at1) \quad \text{[Formula 1]}$$

For each of the plurality of parameters, the interpolation process is executed with Formula 1. In addition, the interpolation coefficient k[t] in Formula 1 may be a coefficient which changes linearly with time as shown in FIG. 4(a) or may be a coefficient which changes in a curve with time as shown in FIG. 4(b). When the coefficient changes in a curve, the curvature of the curve may be set corresponding to, for example, the expansion and contraction movement of the heart. For example, a steep curve may be set in a time period in which the heart shows a rapid movement and a gentle curve may be set in a time period in which the heart shows a moderate movement.

In the case of the coefficient which changes linearly with time as shown in FIG. 4(a), Formula 1 may be transformed into the following formula.

$$k[t]=(1.0/(t1-t0))\cdot t$$

$$a(t)=at1+t\cdot(at0-at1)/(t1-t0) \quad \text{[Formula 2]}$$

Referring again to FIG. 1, when the parameter value at each time from the time of telediastole to the time of telesystole is calculated for each parameter by the parameter calculating unit 48, a region-of-interest setting unit 50 sets, for each time, a three-dimensional region of interest in the three-dimensional data space based on the plurality of parameters. With this process, the three-dimensional region of interest which dynamically changes from the telediastole to the telesystole (refer to FIGS. 2 and 3) is set in the three-dimensional data space. In order to set an ellipsoid in the three-dimensional data space, for example, the following formulas are used.

[Formula 3]

$$\frac{x^2}{a^2}+\frac{y^2}{b^2}+\frac{z^2}{c^2}<1 \quad (1)$$

$$\text{Rot}(x,\theta)=\begin{pmatrix}1 & 0 & 0 & 0\\ 0 & \cos\theta & -\sin\theta & 0\\ 0 & \sin\theta & \cos\theta & 0\\ 0 & 0 & 0 & 1\end{pmatrix} \quad (2)$$

$$\text{Rot}(y,\theta)=\begin{pmatrix}\cos\theta & 0 & \sin\theta & 0\\ 0 & 1 & 0 & 0\\ -\sin\theta & 0 & \cos\theta & 0\\ 0 & 0 & 0 & 1\end{pmatrix} \quad (3)$$

$$\text{Rot}(z,\theta)=\begin{pmatrix}\cos\theta & -\sin\theta & 0 & 0\\ \sin\theta & \cos\theta & 0 & 0\\ 0 & 0 & 1 & 0\\ 0 & 0 & 0 & 1\end{pmatrix} \quad (4)$$

$$\text{Trans}(x0,y0,z0)=\begin{pmatrix}1 & 0 & 0 & x0\\ 0 & 1 & 0 & y0\\ 0 & 0 & 1 & z0\\ 0 & 0 & 0 & 1\end{pmatrix} \quad (5)$$

$$\begin{pmatrix}x_w\\ y_w\\ z_w\\ 1\end{pmatrix}=\begin{pmatrix}1 & 0 & 0 & 100\\ 0 & 1 & 0 & 0\\ 0 & 0 & 1 & 0\\ 0 & 0 & 0 & 1\end{pmatrix}\begin{pmatrix}x_m\\ y_m\\ z_m\\ 1\end{pmatrix}=\begin{pmatrix}x_m+100\\ y_m\\ z_m\\ 1\end{pmatrix} \quad (6)$$

An ellipsoid having a center at the origin and having two minor axis radii of a and c and the major axis radius of b is represented by Equation (1). The rotation and translation of the ellipsoid represented by Equation (1) can be represented with a matrix equation. For example, when the ellipsoid rotates around the x-axis by θ, the matrix equation of Equation (2) is used, when the ellipsoid rotates around the y-axis by θ, the matrix equation of equation (3) is used, and when the ellipsoid rotates around the z-axis by θ, the matrix equation of Equation (4) is used. For translation from the origin to a coordinate (x0, y0, z0), the matrix equation of Equation (5) is used. For example, when the ellipsoid is translated by a coordinate value of 100 along the x-axis, the conversion equation of Equation (6) is used. The region-of-interest setting unit 50 uses, for example, the equations in the Formula 3 and sets the three-dimensional region of interest having the ellipsoidal shape in the three-dimensional data space based on the parameter values of the plurality of parameters at each time.

When the three-dimensional region of interest is set, the cardiac cavity extracting unit 24 extracts echo data of low level in the three-dimensional region of interest. Because the three-dimensional region of interest is suitably set to follow the movement of the heart, the echo data corresponding to the cardiac cavity of the left ventricle is suitably extracted while including a minimum amount of echo data corresponding to the cardiac cavity in sites other than the left ventricle and other low brightness sites. The three-dimensional data in which the cardiac cavity of the left ventricle is extracted at each time is stored in a three-dimensional data memory 26.

A selector 30 selects, for example, according to an instruction of the user, original three-dimensional data stored in the three-dimensional data memory 16 or the three-dimensional data in which the cardiac cavity of the left ventricle is extracted and which is stored in the three-dimensional data memory 26, and sends the selected data to a display image forming unit 32.

The display image forming unit 32 executes a three-dimensional coordinate conversion process and an image process for two-dimensional display as necessary. When the data stored in the three-dimensional data memory 16 is already converted to the rectangular coordinate system as described above, the conversion in this process may include only the process for two-dimensionally displaying the three-dimensional data. Examples of the process for two-dimensional display include a tomographic image formation of orthogonal-three-cross-sections which are set in the three-dimensional image data and a volume rendering process on the three-dimensional image data.

The orthogonal-three-cross-sections are three cross sections which are orthogonal to each other in the data space of the three-dimensional image data, and are, for example, top view, side view, and front view. The display image forming unit 32 extracts, from the three-dimensional image data, the echo data of each cross section of the orthogonal-three-cross-sections, and forms three cross sectional images.

As the volume rendering process, for example, a method disclosed in JP Hei 10-33538 A is preferable. In this method, a viewpoint and a screen are defined sandwiching the three-dimensional data space, and a plurality of rays (sight lines) are defined from the viewpoint to the screen. Then, voxel data (echo data) present on the ray is successively read from the three-dimensional image data for each ray, and a voxel calculation (here, a calculation of amount of output light using opacity based on the volume rendering method) is successively performed on each voxel data. The final voxel calculation result (amount of output light) is converted to a pixel value, and the pixel values of the rays are mapped on the screen, so that a two-dimensional display image is formed which is a display penetrating through the three-dimensional image.

The orthogonal-three-cross-sectional images or the two-dimensional display image by volume rendering formed in the display image forming unit 32 is displayed on the monitor 34. A volume calculating unit 52 calculates a volume (cubic volume) of the cardiac cavity of the left ventricle based on the three-dimensional data stored in the three-dimensional data memory 26. For example, the volume calculating unit 52 calculates the volume of the cardiac cavity of the left ventricle based on the number of echo data corresponding to the cardiac cavity of the left ventricle. The volume is preferably calculated for each time. The calculated volume may be numerically displayed on the monitor 34 or a graph showing the change, as time elapses, of the volume may be displayed.

In the present embodiment, because the plurality of parameters are changed with elapse of time according to the expansion and contraction movement of the heart, the three-dimensional region of interest identified by these parameters can be dynamically and automatically set so that the region of interest follows the expansion and contraction movement of the heart, and further, follow a translational movement and a twisting movement of the heart. In addition, for example, by the user setting the parameter value corresponding to the telediastole of the heart and the parameter value corresponding to the telesystole of the heart, it is possible to very easily set the three-dimensional region of interest which dynamically follows the expansion and contraction movement of the heart, without requiring other complex operations or the like.

The shape of the three-dimensional region of interest is not limited to the ellipsoid. For example, a three-dimensional region of interest having other shapes such as a bullet shape may be used. Alternatively, it is also possible to employ a configuration in which, after the three-dimensional region of interest is automatically set through an interpolation process based on parameters, the user applies a fine adjustment as necessary, to set a more suitable three-dimensional region of interest.

A preferred embodiment of the present invention has been described. The above-described embodiment, however, is merely exemplary in all aspects, and is not intended to limit the scope of the present invention. The present invention includes various modifications that falls in the scope and spirit of the present invention.

What is claimed is:

1. An ultrasound diagnosis apparatus comprising:
   a transmission and reception unit which transmits and receives ultrasound, to collect a plurality of echo data from a three-dimensional space including a heart;
   an image forming unit which forms image data of a three-dimensional ultrasound image including the heart based on the plurality of collected echo data;
   a display unit which displays a three-dimensional ultrasound image corresponding to the formed image data; and
   a region-of-interest setting unit which sets a three-dimensional region of interest for the heart in a three-dimensional data space constructed by the plurality of echo data collected from the three dimensional space, wherein
   the three-dimensional region of interest is identified by a plurality of parameters, and the region-of-interest setting unit determines, for each of the plurality of parameters that identify the three dimensional region of interest, a parameter value at each of a plurality of times between a telediastole and a telesystole based on a parameter value corresponding to the telediastole of the heart and a parameter value corresponding to the telesystole of the heart, and
   the region-of-interest setting unit calculates the parameter value at each of the plurality of times for each of the parameters through an interpolation process using an interpolation coefficient which changes with time corresponding to an expansion and contraction movement of the heart.

2. The ultrasound diagnosis apparatus according to claim 1, wherein
   the region-of-interest setting unit determines the parameter value at each of the plurality of times, so that the plurality of parameters change with time and the three-dimensional region of interest dynamically follows an expansion and contraction movement of the heart.

3. The ultrasound diagnosis apparatus of claim 2, wherein
   the region-of-interest setting unit uses an interpolation coefficient corresponding to a mixture ratio of the parameter value corresponding to the telediastole of the heart and the parameter value corresponding to the telesystole of the heart.

4. The ultrasound diagnosis apparatus according to claim 3, wherein
   the region-of-interest setting unit sets a three-dimensional region of interest, having a shape of an ellipsoid, which is identified by a plurality of parameters including a major axis radius, a minor axis radius, a center coordinate, and a rotation angle.

5. The ultrasound diagnosis apparatus according to claim 2, wherein
   the region-of-interest setting unit sets a three-dimensional region of interest, having a shape of an ellipsoid, which is identified by a plurality of parameters including a major axis radius, a minor axis radius, a center coordinate, and a rotation angle.

6. The ultrasound diagnosis apparatus according to claim 1, wherein
the region-of-interest setting unit uses an interpolation coefficient corresponding to a mixture ratio of the parameter value corresponding to the telediastole of the heart and the parameter value corresponding to the telesystole of the heart.

7. The ultrasound diagnosis apparatus according to claim 6, wherein
the region-of-interest setting unit sets a three-dimensional region of interest, having a shape of an ellipsoid, which is identified by a plurality of parameters including a major axis radius, a minor axis radius, a center coordinate, and a rotation angle.

8. The ultrasound diagnosis apparatus according to claim 1, wherein
the region-of-interest setting unit sets a three-dimensional region of interest, having a shape of an ellipsoid, which is identified by a plurality of parameters including a major axis radius, a minor axis radius, a center coordinate, and a rotation angle.

* * * * *